(12) United States Patent
Yuan et al.

(10) Patent No.: US 10,287,275 B2
(45) Date of Patent: May 14, 2019

(54) 16-MEMBER TRIAMILIDE DERIVATIVES AND USES THEREOF

(71) Applicants: Haiqing Yuan, Irvine, CA (US); Wenjiang Huang, Zhenjiang (CN)

(72) Inventors: Haiqing Yuan, Irvine, CA (US); Wenjiang Huang, Zhenjiang (CN)

(73) Assignee: VICTOR PHARMA CO., LTD. ZHENJIANG, Zhenjiang (CN)

( * ) Notice: Subject to any disclaimer, the term of this patent is extended or adjusted under 35 U.S.C. 154(b) by 532 days.

(21) Appl. No.: 14/789,996

(22) Filed: Jul. 2, 2015

(65) Prior Publication Data

US 2018/0148434 A1 May 31, 2018

Related U.S. Application Data

(60) Provisional application No. 62/148,372, filed on Apr. 16, 2015.

(51) Int. Cl.
| | | |
|---|---|---|
| *C07H 17/08* | (2006.01) | |
| *C07D 405/04* | (2006.01) | |
| *C07D 405/14* | (2006.01) | |
| *A61P 31/04* | (2006.01) | |

(52) U.S. Cl.
CPC ............ *C07D 405/14* (2013.01); *A61P 31/04* (2018.01)

(58) Field of Classification Search
CPC ............................. C07H 17/08; C07D 405/14
USPC .............................................. 536/7.1; 514/30
See application file for complete search history.

(56) References Cited

U.S. PATENT DOCUMENTS 5,545,624 A    8/1996    Hecker et al.

FOREIGN PATENT DOCUMENTS

| CN | 1083068 A    | 3/1994 |
| JP | S59225199 A  | 12/1984 |
| WO | 03/027250 A2 | 4/2003 |

OTHER PUBLICATIONS

Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolynnorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2, p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*

* cited by examiner

*Primary Examiner* — Patricia L Morris
(74) *Attorney, Agent, or Firm* — SZDC Law P.C.

(57) ABSTRACT

The invention discloses 20,23-modified novel derivatives of 16-membered demycarosyltylonolide antibiotics, which are useful against bacterial and mycoplasmic pathogens in humans and animals. Also claimed are pharmaceutical compositions of such derivatives and their use in treating bacterial and mycoplasmic infections in humans and animals.

7 Claims, 1 Drawing Sheet

Figure 1. Chemical structures of Tylosin, Tilmicosin, and Tildipirosin
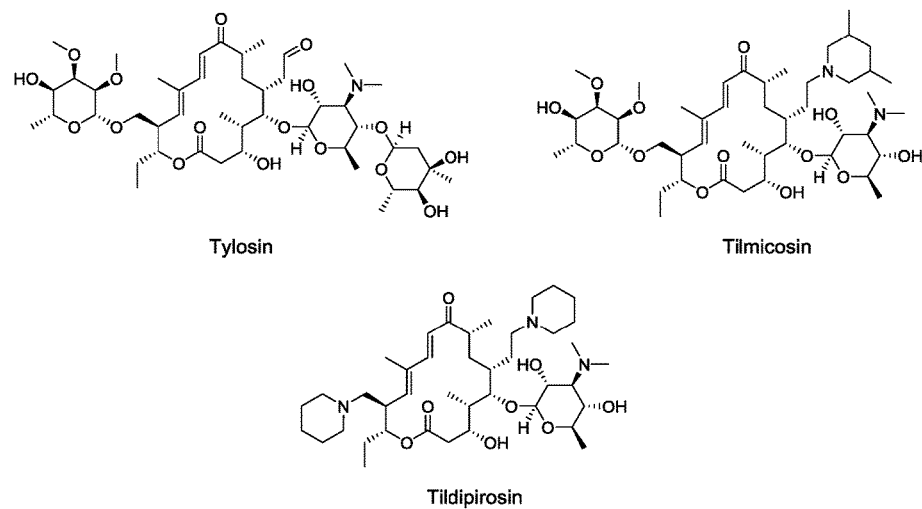
Figure 2. General chemical formulas of the invention compounds.
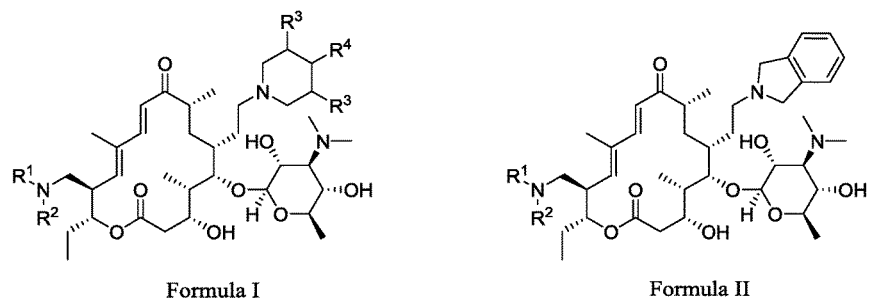
Formula I                    Formula II

16-MEMBER TRIAMILIDE DERIVATIVES AND USES THEREOF

CROSS-REFERENCE TO RELATED APPLICATION

This application claims the priority to U.S. Provisional Application Ser. No. 62/148,372, filed Apr. 16, 2015, which is hereby incorporated by reference in its entirety.

FIELD OF THE INVENTION

The invention relates to novel derivatives of 16-membered triamilide antibiotics, which are useful against bacterial and mycoplasmic pathogens in humans and animals. More specifically, the invention relates to a class of 20,23-modified novel derivatives of 16-membered demycarosyltylonolide, pharmaceutically acceptable salts of such derivatives, the process for preparing such derivatives and the application of such derivatives.

BACKGROUND OF THE INVENTION

Ever since the discovery of penicillin in the 1920s, and streptomycin in the 1940s, many new compounds with antibacterial activity have been discovered and used as antibiotics, which have saved thousands of lives and greatly contributed to the development of modern animal husbandry industry. But over time, bacteria can become resistant to existing drugs, making infections difficult to treat or even impossible to control. Currently, antibiotic-resistant bacteria has become a growing public health threat, as exemplified by the long-existing Methicillin-resistant *Staphylococcus aureus* (MRSA) and the recent emergence of NDM-1 superbugs. In fact, almost all of the clinical used antibiotics have been found to eventually lead to the emergence of resistant bacteria strains, such as drug-resistant strains of Gram-positive bacteria, methicillin-resistant *staphylococcus*, *streptococcus*, penicillin-resistant and vancomycin-resistant *enterococci*, etc. When these resistant bacteria infect patients or animals they cause serious or even fatal consequences. In the field of drug research the development of new antibiotics is an important way to combat the problem of drug-resistant.

Macrolides are a class of 14-16 membered lactone antibiotics substituted with one or more deoxy sugars, including erythromycin, tylosin, tilmicosin, roxithromycin, erythromycin, azithromycin, clarithromycin, spiramycin, tulathromycin, oleandomycin, carbomycin, and flurithromycin, etc. Macrolides exert their bacteriostatic effect by binding reversibly to the P site on the subunit 50S of the bacterial ribosome, inhibiting bacterial protein synthesis through preventing peptidyltransferase from adding the growing peptide attached to tRNA to the next amino acid, as well as inhibiting ribosomal translation, similarly to the mechanism of action of chloramphenicol and lincosamides antibiotics. Another potential mechanism is premature dissociation of the peptidyl-tRNA from the ribosome.

Macrolide antibiotic resistant bacteria also have emerged. The mechanisms of resistance include: (1) by reducing the permeability of the bacterial cell wall or acquired efflux mechanism to reduce drug accumulation in cells; (2) by ermA, ermB and ermC gene mediated methylation of 50S ribosome binding sites, thereby greatly reducing the affinity of antimicrobial agents to the ribosome binding site; (3) enzymatic inactivation of the drug by the bacteria due to induced production of ester hydrolase.

Tylosin and its associated 16-membered macrolide derivatives (see FIG. 1) have already proven to be effective against certain infections caused by Gram-positive and Gram-negative bacteria in animals such as poultry, cattle, and pigs. (Kirst et. al., U.S. Pat. Nos. 4,468,511, 4,920,103; Tao et. al., U.S. Pat. No. 4,921,947; Lukacs et. al., U.S. Pat. No. 5,032,581). The chemical structures of Tylosin, Tilmicosin, and Tildipirosin are shown in FIG. 1. However, tylosin suffers relatively low bioavailability, gastrointestinal side effects, and limited spectrum of antibacterial activity. Tilmicosin is a 20-modified tylosin derivative with significantly improved pharmacokinetic properties, especially the longer half-life (U.S. Pat. No. 5,545,624). Its main disadvantage is cardiac toxicity, particularly when administered by injection.

Another tylosin related macrolide derivative Tildipirosin retained the piperidinyl base substructure of the tilmicosin at the 20-position but further modified the substituent at position 23, replacing the mycinose with another piperidinyl ring, resulted in higher activity against *Mannheimia haemolytica* and *Pasteurella multocida*, which are the two main etiological agents of bovine respiratory disease (U.S. Pat. No. 6,514,946 B1). Tildipirosin and Tulathromycin both contain three basic amino groups, which could contribute to the enrichment in the lung tissue and bronchoalveolar fluid and the longer half-life of these triamilides. However, while two identical piperidines at positions 20 and 23 may have improved the efficacy against certain pathogens and circumvented stereoisomeric issues of the 20-dimethylpiperidine in Tilmicosin, novel modifications at positions 20 and 23 could potentially provide agents of further improved antibacterial profile and reduced resistance. Stephen Douthwaite et al have recently studied the inhibition of protein synthesis on the bacterial ribosome by tylosin related macrolides and suggested that positions 20 and 23 of the macrolide molecules are closely associated with nucleotide A2058 and G748 for binding affinity, where mutation or methylation are responsible for the observed resistance (Antimicrob. Agents Chemother. 2012, 56(11):6033). It has also been suggested by a computer assisted modeling study that the interaction of 23-piperidine of Tildipirosin with the binding tunnel is slightly more distal from G748 (ACS Chem. Biol. 2012, 7, 1351-1355) and we believe that the protonation state of the piperidine nitrogen is also critical to the binding affinity.

A variety of structural modifications of tylosin macrolide have been reported over the years, for example, U.S. Pat. No. 4,468,511A, GB2135670A, U.S. Pat. No. 6,514,946, and references therein described 20- and 23-modified tylosin macrolides. More recently, Hong Fu et al described tylonolide 9- and 20-modified derivatives with ketolide-like activity against macrolide-resistant *S. pneumoniae* and inducible-resistant *S. aureus* strains in vitro. (Bioorganic & Medicinal Chemistry Letters 2006, 16, 1259-1266).

SUMMARY OF THE INVENTION

The invention provides a class of novel 20-, 23-modified 16-membered tylonolide antibiotic compounds represented by general Formula I or general Formula II (FIG. 2) or a pharmaceutically acceptable salt thereof:

Wherein:
  $R^1$ is a group comprising optionally substituted $C_{1-6}$ alkyl or $C_{3-8}$ cycloalkyl, where the substituent is selected from aryl or hydroxyl;
  $R^2$ is a group comprising hydrogen, optionally substituted $C_{1-6}$ alkyl or $C_{3-8}$ cycloalkyl, where the substituent is selected from aryl or hydroxyl;

Or R¹ and R² are bonded covalently so that R¹—N—R² forms an optionally substituted 3-5 membered or 7-9 membered heterocyclic ring, where the substituent is selected from $C_{1-3}$ alkyl or hydroxyl;

R³ and R⁴ are independently selected from a group comprising hydrogen or $C_{1-3}$ alkyl.

In one aspect, the invention provides a compound having Formula I or Formula II wherein R¹ is optionally substituted $C_{1-4}$ alkyl or $C_{3-8}$ cycloalkyl, where the substituent is selected from benzene, pyridine or hydroxyl.

In another aspect, the invention provides a compound having Formula I or Formula II wherein R¹ is optionally substituted $C_{1-2}$ alkyl group, where the substituent is selected from benzene, pyridine or hydroxyl.

In another aspect, the invention provides a compound having Formula I or Formula II wherein R¹ is ethyl, n-propyl, isopropyl, butyl, benzyl, 2-hydroxyethyl, 2-pyridylmethyl, 3-pyridylmethyl, 4-pyridylmethyl, or cyclohexyl.

In another aspect, the invention provides a compound having Formula I or Formula II wherein R² is hydrogen or an optionally substituted $C_{1-4}$ alkyl group, where the substituent is selected from benzene, pyridine or hydroxyl.

In another aspect, the invention provides a compound having Formula I or Formula II wherein R² is hydrogen or an optionally substituted $C_{1-2}$ alkyl group, where the substituent is selected from benzene, pyridine or hydroxyl.

In another aspect, the invention provides a compound having Formula I or Formula II wherein R² is hydrogen, methyl, ethyl, n-propyl, isopropyl, n-butyl or 2-hydroxyethyl.

In another aspect, the invention provides a compound having Formula I or Formula II wherein R¹ and R² are bonded covalently so that R¹—N—R² forms an optionally substituted 5-membered or 9-membered heterocyclic ring, where the substituent is selected from methyl, ethyl, n-propyl, isopropyl or hydroxyl.

In another aspect, the invention provides a compound having Formula I or Formula II wherein R¹ and R² are bonded covalently so that R¹—N—R² forms tetrahydropyrrolyl, 3-hydroxy-pyrrolidinyl, 3,5-dimethyl-piperidinyl, or isoindoline group.

In another aspect, the invention provides a compound having Formula I or Formula II wherein R³ and R⁴ are independently selected from hydrogen or methyl.

Unless otherwise stated, the following terms used in the specification and claims have the meanings discussed below:

The term "alkyl", as used herein, refers to saturated, monovalent or divalent hydrocarbon 123 moieties having linear or branched moieties or combinations thereof and containing 1 to 6 carbon 124 atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Hydrogen atoms on alkyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups.

The term "aryl" as used herein, refers to an organic moiety derived from an aromatic hydrocarbon consisting of a ring containing 6 to 10 carbon atoms by removal of one hydrogen. Aryl can be monocyclic or polycyclic. Aryl can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups. Non-limiting examples of aryl groups are phenyl, pyridyl, pyrrolyl, furyl, thienyl, imidazolyl, oxazolyl, thiazolyl, pyrazolyl, pyrimidinyl, quinolinyl, isoquinolinyl, purinyl, tetrazolyl, triazinyl, naphthyl and anthryl.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be interrupted by a C=O; the S heteroatom can be oxidized. Heterocycles can be monocyclic or polycyclic. Heterocyclic ring moieties can be substituted by groups including, but not limited to: halogens, —OH, C 3-8 cycloalkyl, non-aromatic heterocycles, aromatic heterocycles, —OC1-6 alkyl, —NH2, —NO2, amides, ethers, esters, aldehydes, sulfonamides groups. Non-limiting examples of unsubstituted heterocycles are pyrrolidinyl, piperidinyl, piperazinyl, morpholinyl, thiomorpholinyl, indolinyl, isoindolinyl.

The term "hydroxyl" as used herein, represents a group of formula "—OH".

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I or Formula II are able to form.

The acid addition salt form of a compound of Formula I or Formula II that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta—Zürich, 2002, 329-345). Compounds of Formula I or Formula II and their salts can be in the form of a solvate, which is included within the scope of the invention. Such solvates include for example hydrates, alcoholates and the like.

With respect to the invention reference to a compound or compounds, is intended to encompass that compound in each of its possible isomeric forms and mixtures thereof unless the particular isomeric form is referred to specifically.

Compounds according to the invention may exist in different polymorphic forms. Although not explicitly indicated in the above formula, such forms are intended to be included within the scope of the invention.

Some compounds of the invention are:
(4R,5S,6S,7R,9R,11E,13E,15R,16R)-15-((diethylamino) methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl) ethyl)oxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-15-((dipropylamino)methyl)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-15-((butylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)-15-(pyrrolidin-1-ylmethyl)oxacyclohexadeca-11,13-diene-2,10-dione;

(4R,5S,6S,7R,9R,11E,13E,15R,16R)-15-((benzylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-15-((benzyl(methyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-15-((bis(2-hydroxyethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-15-((cyclohexylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-15-((benzyl(ethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-15-((benzyl(isopropyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-15-((methyl(pyridin-3-ylmethyl)amino)methyl)-7-(2-(piperidin-1-yl)ethyl)oxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-15-(isoindolin-2-ylmethyl)-5,9,13-trimethyl-7-(2-(piperidin-1-yl)ethyl)oxacyclohexadeca-11,13-diene-2,10-dione;

(4R,5S,6S,7R,9R,11E,13E,15R,16R)-15-((benzyl(isopropyl)amino)methyl)-6-(((2R,3R,4S,5S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-5,9,13-trimethyloxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-5,9,13-trimethyl-15-((methyl(pyridin-3-ylmethyl)amino)methyl)oxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-15-(isoindolin-2-ylmethyl)-5,9,13-trimethyloxacyclohexadeca-11,13-diene-2,10-dione;

(4R,5S,6S,7R,9R,11E,13E,15R,16R)-15-((benzyl(methyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-7-(2-(isoindolin-2-yl)ethyl)-5,9,13-trimethyloxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-7-(2-(isoindolin-2-yl)ethyl)-5,9,13-trimethyl-15-(piperidin-1-ylmethyl)oxacyclohexadeca-11,13-diene-2,10-dione;

(4R,5S,6S,7R,9R,11E,13E,15R,16R)-15-((diethylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-7-(2-(isoindolin-2-yl)ethyl)-5,9,13-trimethyloxacyclohexadeca-11,13-diene-2,10-dione;

(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-15-((3,5-dimethylpiperidin-1-yl)methyl)-16-ethyl-4-hydroxy-7-(2-(isoindolin-2-yl)ethyl)-5,9,13-trimethyloxacyclohexadeca-11,13-diene-2,10-dione.

The invention also provides processes for preparing a compound of formula I or formula II that comprises the following steps:

(1) Reductive amination of tylosin and concurrent removal of mycarose. Tylosin and appropriately substituted piperidine or isoindoline react in the presence of formic acid to form Intermediate 1a or 1b;

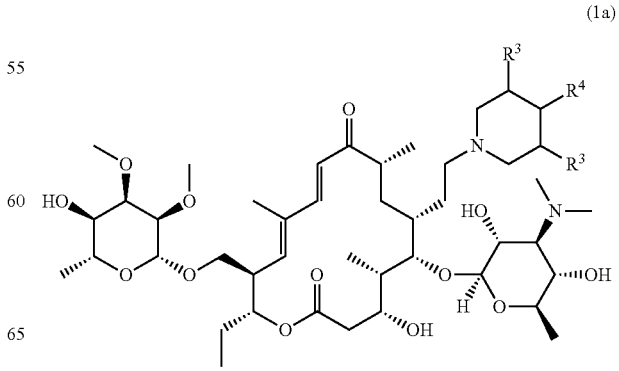

(1a)

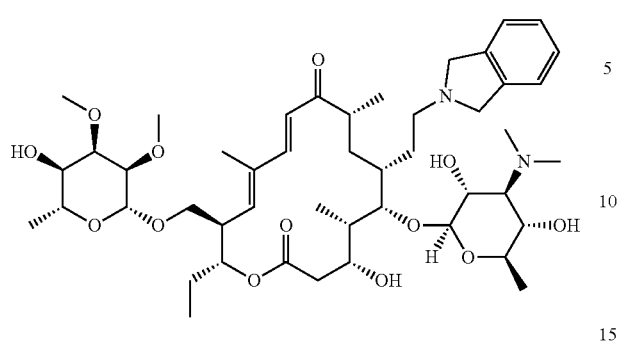
(2) Removal of mycinose. Intermediate 1a or 1b reacts with inorganic acids to form Intermediate 2a or 2b;
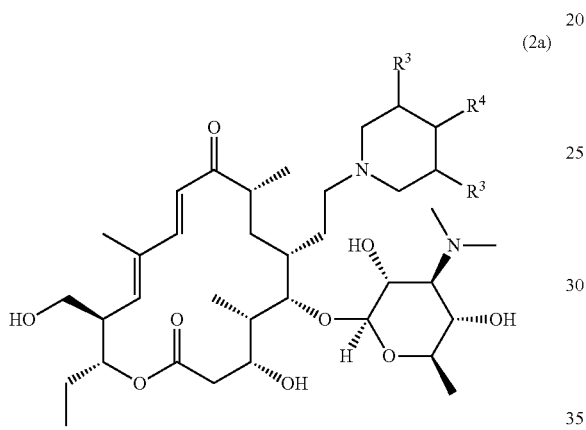
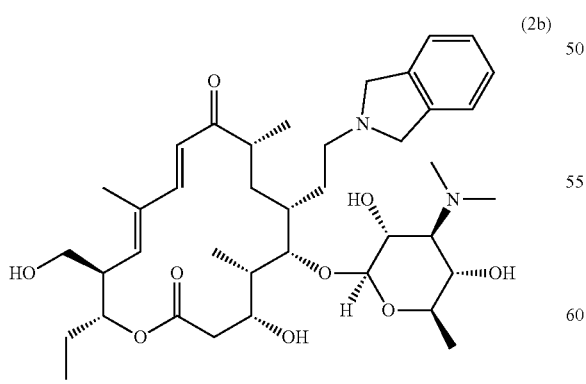
(3) Activation of the intermediate 2a or 2b by reacting with iodine, triphenylphosphine, and pyridine to form Intermediate 3a or 3b;
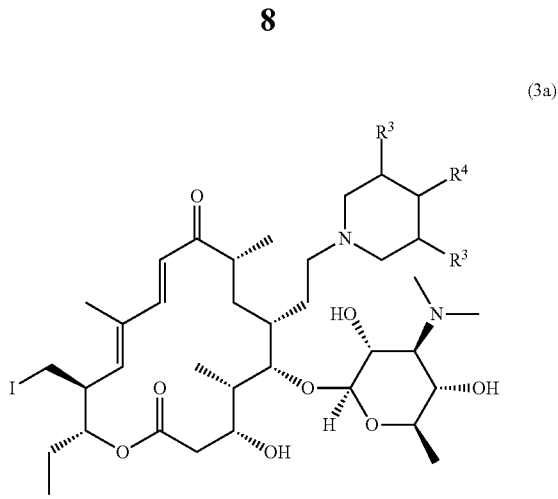
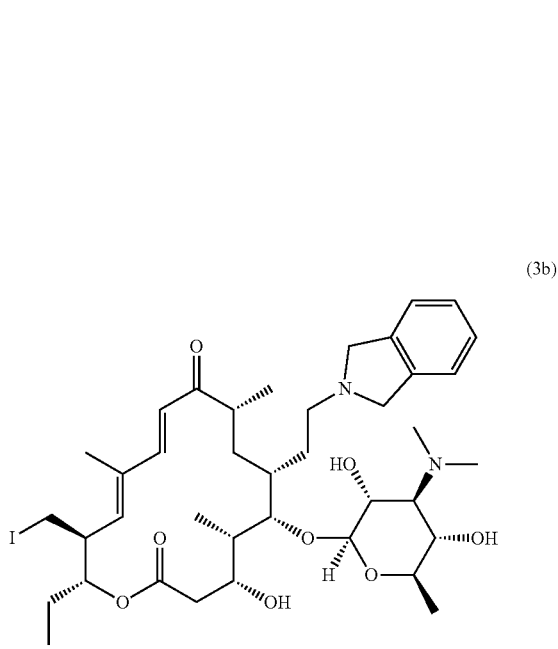
(4) Amination of Intermediate 3a or 3b under basic conditions with an organic amine to form compounds of formula I or formula II.
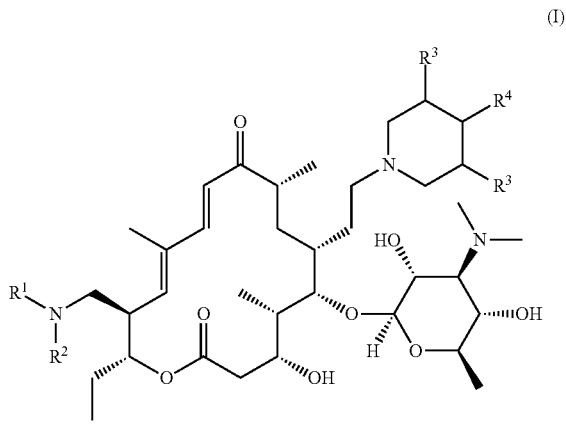

-continued

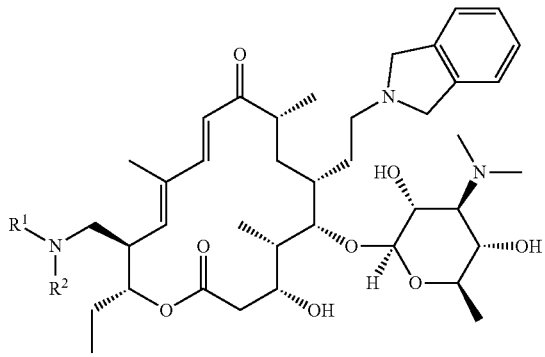

(II)

Groups $R^1$, $R^2$, $R^3$, and $R^4$ in the above formulas are as defined above. Preferably, reaction step (1) is carried out using formic acid in toluene or dioxane at 70~85° C.; in reaction step (2) the inorganic acid is hydrobromic acid, and the reaction temperature is 50° C.~60° C.; in step (3), the reaction solvent is methylene chloride and the reaction temperature is 0~20° C.; in reaction step (4) the base used is selected from potassium carbonate, sodium carbonate, or triethylamine, with or without solvent, and the reaction temperature is 25~140° C.

Those skilled in the art will be able to routinely modify and/or adapt the above steps to synthesize any compounds of the invention covered by Formula I or Formula II.

In another aspect, there are provided pharmaceutical compositions including at least one compound of the invention in a pharmaceutically acceptable carrier.

In another aspect, there are provided a method for using the above compounds for the treatment and prevention of bacterial infection and mycoplasma infection in a human or animal (including mammals, fish and birds). These disorders in a human or animal include, but are not limited to: bovine respiratory disease (BRD) caused by *Pasteurella haemolytica*, *Pasteurella multocida* and *Haemophilus somnus*, pasteurellosis in pigs, goats, sheep and poultry caused by *Pasteurella multocida*, porcine contagious pleuropneumonia and streptococcal infection caused by *Actinobacillus*, and mycoplasma infections in cattle, pigs, goats, sheep and poultry.

BRIEF DESCRIPTION OF THE DRAWINGS

FIG. 1 depicts the chemical structures of Tylosin, Tilmicosin, and Tildipirosin.

FIG. 2 depicts the general chemical formulas of the invention compounds.

DETAILED DESCRIPTION OF THE INVENTION

The invention is illustrated by the following examples. However, the invention is not limited to the specific details of the following embodiments. It will be understood by those skilled in the art that the invention extends beyond the specifically disclosed embodiments to other alternative embodiments and/or uses of the invention and obvious modifications and equivalents thereof. Thus, it is intended that the scope of the invention herein disclosed should not be limited by the particular disclosed embodiments described below, but should be determined only by a fair reading of the claims that follow.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diasteroisomeric isomers, chromatographic separation may be employed.

Compound names were generated with ChemBioDraw version 12. The general chemical formulas of the invention compounds are shown in FIG. 2.

Unless specified otherwise, all reagents, solvents, catalysts for which the synthesis is not described are purchased from commercial sources and used as received. Air and/or moisture-sensitive reactions were run under an Ar- or $N_2$-atmosphere. Isolation and purification of compounds can be accomplished by chromatography, such as thin layer chromatography on silica gel, HG/T2354-92, GF254, Qingdao Ocean Chemical Co.; sodium carboxymethyl cellulose, 300-800 mPa·S, Catalog #30036328, Sinopharm Chemical Reagent Co., Ltd., 300-400 mesh silica gel preparative plates.

Structural Identification of compounds of the invention can be accomplished by NMR and mass spectrometry. Such as the 300-Bruker NMR spectrometer; SHIMADZU LCMS-2020, ESI source.

Example 1

Intermediate 1

(4R,5S,6S,7R,9R,11E,13E,15R,16R)-6-(((2R,3R,4S,5S,6R)-4-(dimethylamino)-3,5-dihydroxy-6-methyl-tetrahydro-2H-pyran-2-yl)oxy)-16-ethyl-4-hydroxy-15-(((((2R,3R,4R,5R,6R)-5-hydroxy-3,4-dimethoxy-6-methyltetrahydro-2H-pyran-2-yl)oxy)methyl)-5,9,13-trimethyl-7-(2-(piperidin-1-yl)ethyl)oxacyclohexadeca-11,13-diene-2,10-dione

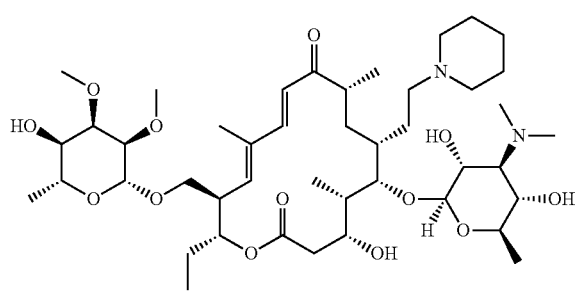 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CO[C@@H]1O[C@H](C)[C@@H](O)[C@@H](OC)[C@H]1OC]

To a stirred solution of tylosin (9.2 g, 0.010 mol) and piperidine (2.55 g, 0.030 mol) in toluene (30 ml) at 75° C. was slowly added formic acid (2.5 g, 0.054 mol) dropwise, the reaction was continued at 75-80° C. for 2 hours. After completion the reaction was extracted with dilute hydrochloric acid (15%, 90 ml) three times. The combined aqueous layer was basified with 30% aqueous sodium hydroxide solution to pH 10, the resulting white precipitate was filtered and washed with water and dried in vacuo to afford the crude title compound (9.0 g). Mass Calcd: 840.53, Found: 841.45 (M+H$^+$).

Example 2

Intermediate 2

(4R,5S,6S,7R,9R,11E,13E,15R,16R)-6-(((2R,3R,4S,5S,6R)-4-(dimethylamino)-3,5-dihydroxy-6-methyl-tetrahydro-2H-pyran-2-yl)oxy)-16-ethyl-4-hydroxy-15-(hydroxymethyl)-5,9,13-trimethyl-7-(2-(piperidin-1-yl)ethyl)oxacyclohexadeca-11,13-diene-2,10-dione

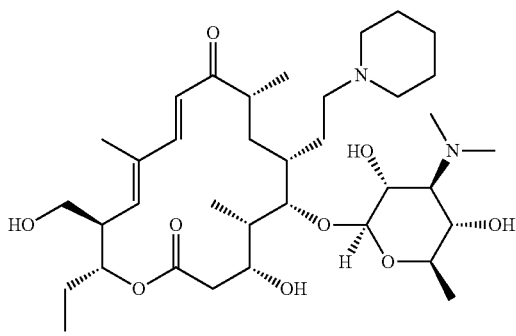 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CO]

A solution of Intermediate 1 (9.0 g, 0.010 mol) in hydrobromic acid (30 ml) and water (30 ml) was stirred at 57° C. for 5 hours. The mixture was cooled to room temperature and was filtered. The filtrate with basified with 30% sodium hydroxide solution to ~pH 10, the resulting precipitate was filtered and dried in vacuo to afford the crude title compound (4.7 g). Mass Calcd: 666.45, Found: 667.40 (M+H$^+$).

Example 3

Intermediate 3

(4R,5S,6S,7R,9R,11E,13E,15S,16R)-6-(((2R,3R,4S,5S,6R)-4-(dimethylamino)-3,5-dihydroxy-6-methyl-tetrahydro-2H-pyran-2-yl)oxy)-16-ethyl-4-hydroxy-15-(iodomethyl)-5,9,13-trimethyl-7-(2-(piperidin-1-yl)ethyl)oxacyclohexadeca-11,13-diene-2,10-dione

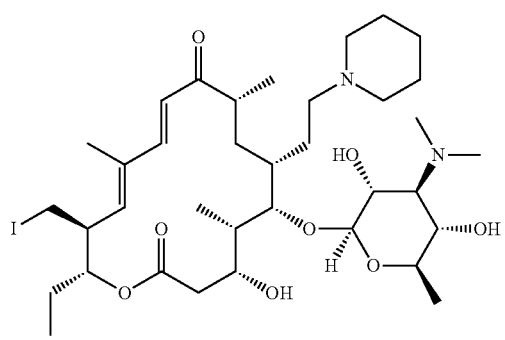 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CI]

To a mixture of Intermediate 2 (12.4 g, 0.019 mol), triphenylphosphine (8.0 g, 0.031 mol), and pyridine (2.0 g, 0.025 mol) in dichloromethane (40 ml) in an ice bath was added iodine (8.0 g, 0.031 mol) portionwise while maintaining the reaction temperature under 15±3° C. The reaction was continued at this temperature for 3 hours and was filtered, the filtrate was extracted twice with 30 ml of 15% hydrochloric acid, and the combined aqueous layer was basified with 30% sodium hydroxide solution to pH 9-10, the resulting off-white precipitate was filtered and dried. The crude product was dissolved in a minimal amount of methylene chloride, and was crystallized from petroleumether to afford the title compound (8.7 g). Mass Calcd: 776.35, Found: 777.70 (M+H$^+$).

Example 4

Compounds 4a-4l

Organic amines, toluene, 1,4-dioxane were dried over anhydrous sodium sulfate prior to use; triethylamine was dried and freshly distilled.

Method A: A mixture of Intermediate 3 (0.5 g), an organic amine (1 ml), and triethylamine (1 ml) in toluene (2 ml) was heated at reflux under nitrogen for 24-48 hours, cooled to room temperature, concentrated under reduced pressure, and the crude product was purified by preparative thin layer chromatography (ethyl acetate:chloroform:methanol=1:1:1 (v/v/v), yield 50%-60%).

Method B: A mixture of Intermediate 3 (1.0 g), anhydrous potassium carbonate (0.2 g), and an organic amine (2-10 ml) was stirred under nitrogen at 25-140° C. until the starting material was consumed (TLC detection). The excess organic amine was removed under reduced pressure, and the residue was triturated with petroleumether to afford the crude title compound. Pure material was purified by preparative thin layer chromatography.

Method C: A mixture of Intermediate 3 (0.5 g), anhydrous potassium carbonate (0.1 g), and an organic amine (5 equivalents) in 1,4-dioxane (10 ml) was stirred under nitrogen at 110° C. until the starting material was consumed (TLC detection). The solvent was removed under reduced pressure, and the residue was triturated with petroleumether to afford the crude title compound. Pure material was purified by preparative thin layer chromatography.

Compounds 4a-4l were prepared according to Method A or Method B or Method C.

| Cmpd # | Compound Name | Structure | MS |
|---|---|---|---|
| 4a | (4R,5S,6S,7R,9R,11E,13E,15R,16R)-15-(((diethylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 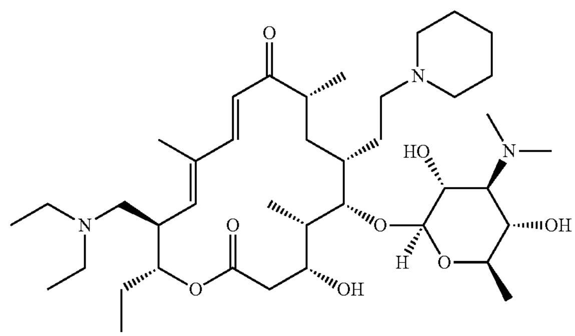 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CN(CC)CC] | 722.50 (M + H$^+$) |
| 4b | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-15-((dipropylamino)methyl)-16-ethyl-4-hydroxy-5,9,13-trimethyl-7-(2-(piperidin-1-yl)ethyl)oxacyclohexadeca-11,13-diene-2,10-dione | 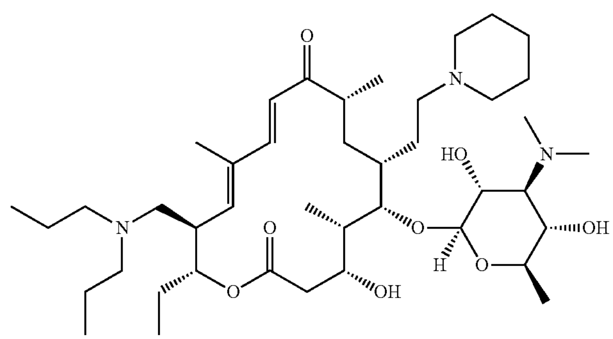 [SMILES: CCCN(CCC)C[C@H]1/C=C(C)/C=C/C(=O)[C@H](C)C[C@H](CCN2CCCCC2)[C@H](O[C@@H]2O[C@H](C)[C@@H](O)[C@H](N(C)C)[C@H]2O)[C@@H](C)[C@H](O)CC(=O)O[C@@H]1CC] | 750.55 (M + H$^+$) |
| 4c | (4R,5S,6S,7R,9R,11E,13E,15R,16R)-15-((butylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 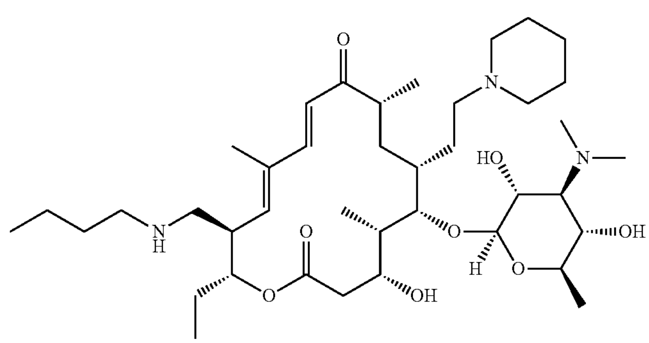 | 740.55 (M + H$_3$O$^+$) |
| 4d | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)-15-(pyrrolidin-1-ylmethyl)oxacyclohexadeca-11,13-diene-2,10-dione | 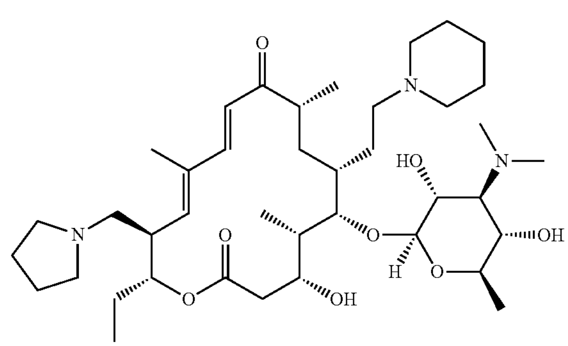 | 738.50 (M + H$_3$O$^+$) |

-continued

| Cmpd # | Compound Name | Structure | MS |
|---|---|---|---|
| 4e | (4R,5S,6S,7R,9R,11E,13E,15R,16R)-15-((benzylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 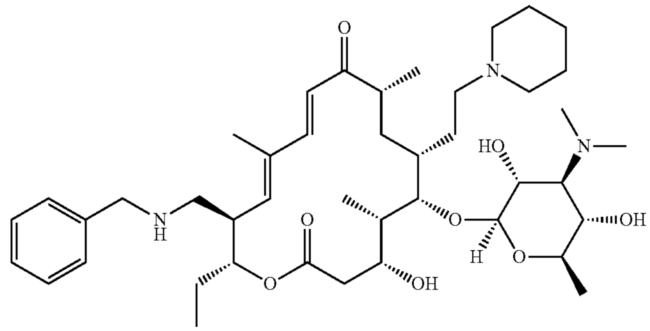 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CNCc1ccccc1] | 778.45 (M + Na$^+$) |
| 4f | (4R,5S,6S,7R,9R,11E,13E,15R,16R)-15-((benzyl(methyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 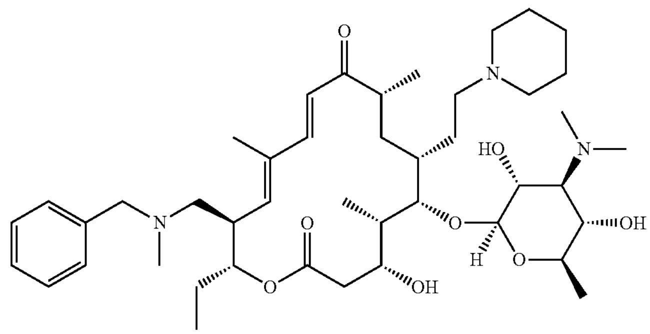 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CN(C)Cc1ccccc1] | 770.50 (M + H$^+$) |
| 4g | (4R,5S,6S,7R,9R,11E,13E,15R,16R)-15-((bis(2-hydroxyethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 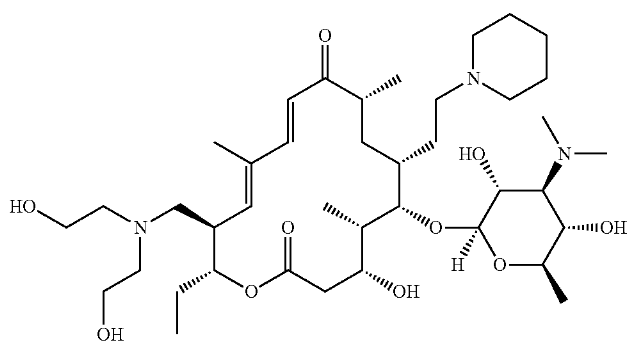 | 772.50 (M + H$_3$O$^+$) |
| 4h | (4R,5S,6S,7R,9R,11E,13E,15R,16R)-15-((cyclohexylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 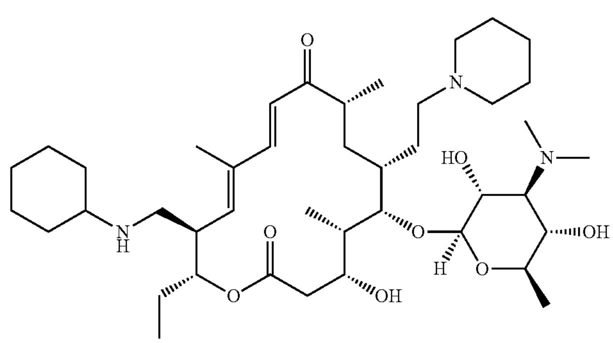 | 788.60 (M + H$_2$O + Na$^+$) |

| Cmpd # | Compound Name | Structure | MS |
|---|---|---|---|
| 4i | (4R,5S,6S,7R,9R,11E,13E,15R,16R)-15-((benzyl(ethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 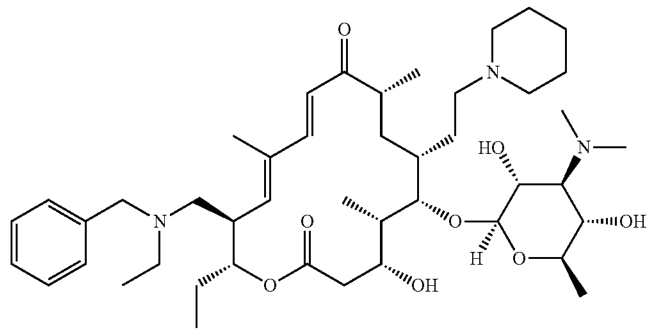 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CN(CC)Cc1ccccc1] | 784.50 (M + H⁺) |
| 4j | (4R,5S,6S,7R,9R,11E,13E,15R,16R)-15-((benzyl(isopropyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione | 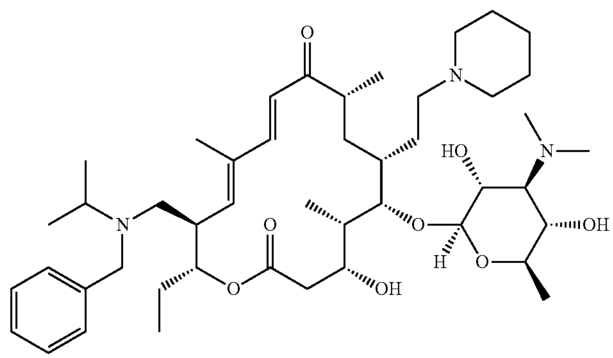 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CN(Cc1ccccc1)C(C)C] | 798.55 (M + H⁺) |
| 4k | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-15-((methyl(pyridin-3-ylmethyl)amino)methyl)-7-(2-(piperidin-1-yl)ethyl)oxacyclohexadeca-11,13-diene-2,10-dione | 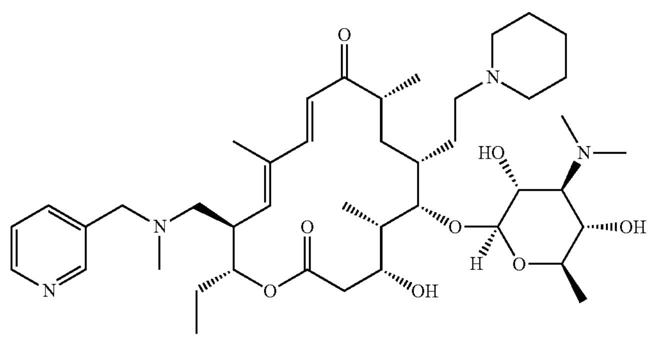 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CN(C)Cc1cccnc1] | 771.50 (M + H⁺) |
| 4l | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-15-(isoindolin-2-ylmethyl)-5,9,13-trimethyl-7-(2-(piperidin-1-yl)ethyl)oxacyclohexadeca-11,13-diene-2,10-dione | 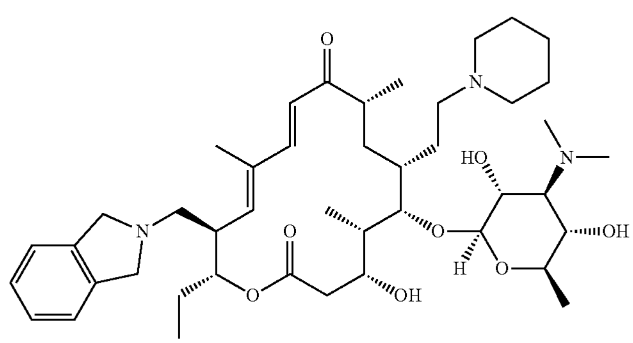 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CCCCC2)C[C@@H](C)C(=O)/C=C/C(C)=C/[C@@H]1CN1Cc2ccccc2C1] | 768.45 (M + H⁺) |

Example 5

Intermediate 5

(4R,5S,6S,7R,9R,11E,13E,15R,16R)-6-(((2R,3R,4S,5S,6R)-4-(dimethylamino)-3,5-dihydroxy-6-methyl-tetrahydro-2H-pyran-2-yl)oxy)-7-(2-(3,5-dimethylpi-peridin-1-yl)ethyl)-16-ethyl-4-hydroxy-15-((((2R,3R,4R,5R,6R)-5-hydroxy-3,4-dimethoxy-6-methyltetrahydro-2H-pyran-2-yl)oxy)methyl)-5,9,13-trimethyloxacyclohexadeca-11,13-diene-2,10-dione

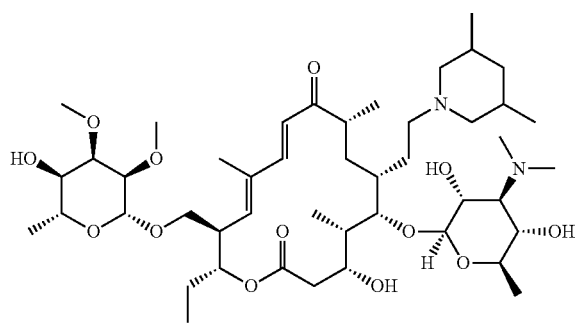 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CC(C)CC(C)C2)C[C@@H](C)C(=O)/C=C/C(C)=C/[C@@H]1CO[C@@H]1O[C@H](C)[C@@H](O)[C@@H](OC)[C@H]1OC]

To a stirred solution of tylosin (19 g, 0.021 mol) and 3,5-dimethylpiperidine (6.8 g, 0.060 mol) in toluene (60 ml) at 75° C. was slowly added formic acid (4.6 g, 0.10 mol) dropwise, the reaction was continued at 75-80° C. for 2 hours. After completion the reaction was extracted with dilute hydrochloric acid (15%, 180 ml) three times. The combined aqueous layer was basified with 30% aqueous sodium hydroxide solution to ~pH 10, the resulting white precipitate was filtered and washed with water and dried in vacuo to afford the crude title compound (22.5 g). Mass Calcd: 868.57, Found: 869.55 (M+H$^+$).

Example 6

Intermediate 6

(4R,5S,6S,7R,9R,11E,13E,15R,16R)-6-(((2R,3R,4S,5S,6R)-4-(dimethylamino)-3,5-dihydroxy-6-methyl-tetrahydro-2H-pyran-2-yl)oxy)-7-(2-(3,5-dimethylpi-peridin-1-yl)ethyl)-16-ethyl-4-hydroxy-15-(hydroxymethyl)-5,9,13-trimethyloxacyclohexadeca-11,13-diene-2,10-dione

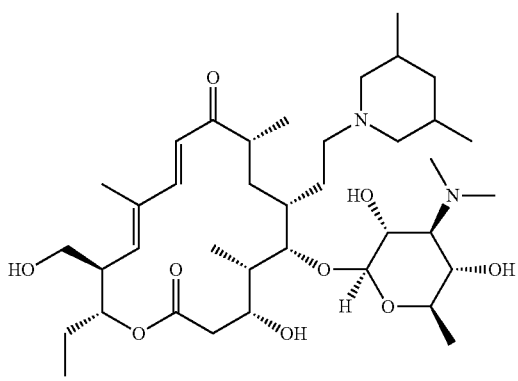 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CC(C)CC(C)C2)C[C@@H](C)C(=O)/C=C/C(C)=C/[C@@H]1CO]

A solution of Intermediate 5 (22.5 g, crude, ~0.021 mol) in hydrobromic acid (30 ml) and water (30 ml) was stirred at 57° C. for 4 hours. The mixture was cooled to room temperature and was filtered. The filtrate with basified with 30% sodium hydroxide solution to ~pH 10, the resulting gummy precipitate was taken out and was triturated with brine, filtered and dried in vacuo to afford the title compound (15 g). Mass Calcd: 694.48, Found: 695.45 (M+H$^+$).

Example 7

Intermediate 7

(4R,5S,6S,7R,9R,11E,13E,15S,16R)-6-(((2R,3R,4S,5S,6R)-4-(dimethylamino)-3,5-dihydroxy-6-methyl-tetrahydro-2H-pyran-2-yl)oxy)-7-(2-(3,5-dimethylpi-peridin-1-yl)ethyl)-16-ethyl-4-hydroxy-15-(iodomethyl)-5,9,13-trimethyloxacyclohexadeca-11,13-diene-2,10-dione

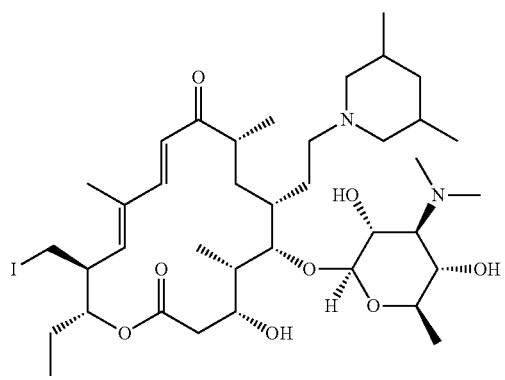 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CC(C)CC(C)C2)C[C@@H](C)C(=O)/C=C/C(C)=C/[C@@H]1CI]

To a mixture of Intermediate 6 (15 g, ~0.021 mol), triphenylphosphine (13 g, 0.050 mol), and pyridine (3.2 g, 0.042 mol) in dichloromethane (60 ml) in an ice bath was added iodine (13 g, 0.051 mol) portionwise while maintaining the reaction temperature under 15±3° C. The reaction was continued at this temperature for 4 hours and was filtered, the filtrate was extracted three times with 15 ml of concentrated hydrochloric acid, and the combined aqueous layer was basified with 30% sodium hydroxide solution to pH 9-10, the resulting off-white precipitate was filtered and dried. The crude product was dissolved in 20 ml water and was triturated with brine. The crude product can be further purified by crystallization from petroleumether to afford the title compound (7.3 g). Mass Calcd: 804.38, Found: 805.35 (M++H$^+$).

Example 8

Compounds 8a-8c

Compounds 8a-8c were prepared from Intermediate 7 using Method B as described in Example 4.

| Cmpd # | Compound Name | Structure | MS |
|---|---|---|---|
| 8a | (4R,5S,6S,7R,9R,11E,13E,15R,16R)-15-((benzyl(isopropyl)amino)methyl)-6-(((2R,3R,4S,5S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-5,9,13-trimethyloxacyclohexadeca-11,13-diene-2,10-dione | 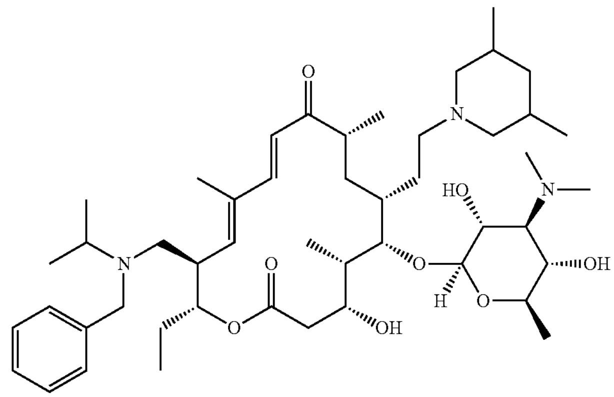 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CC(C)CC(C)C2)C[C@@H](C)C(=O)/C=C/C(C)=C/[C@@H]1CN(Cc1ccccc1)C(C)C] | 826.55 (M + H+) |
| 8b | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-5,9,13-trimethyl-15-((methyl(pyridin-3-ylmethyl)amino)methyl)oxacyclohexadeca-11,13-diene-2,10-dione | 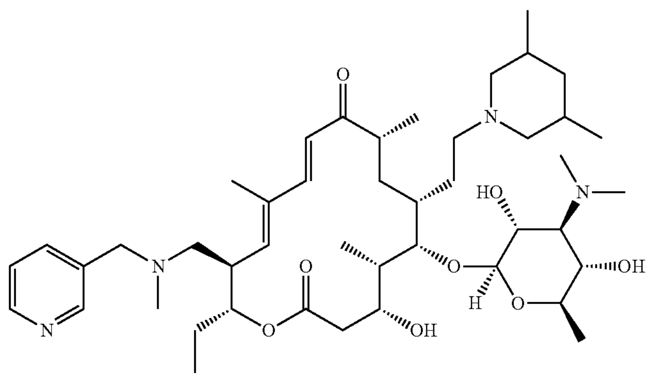 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CC(C)CC(C)C2)C[C@@H](C)C(=O)/C=C/C(C)=C/[C@@H]1CN(C)Cc1cccnc1] | 799.50 (M + H+) |
| 8c | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-15-(isoindolin-2-ylmethyl)-5,9,13-trimethyloxacyclohexadeca-11,13-diene-2,10-dione | 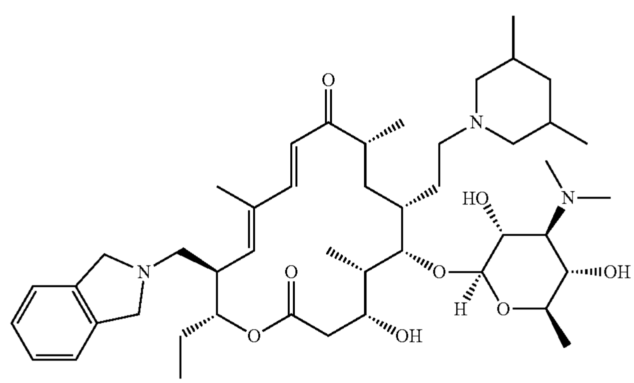 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2CC(C)CC(C)C2)C[C@@H](C)C(=O)/C=C/C(C)=C/[C@@H]1CN1Cc2ccccc2C1] | 796.50 (M + H+) |

Example 9

Intermediate 9

(4R,5S,6S,7R,9R,11E,13E,15R,16R)-6-(((2R,3R,4S,
5S,6R)-4-(dimethylamino)-3,5-dihydroxy-6-methyl-
tetrahydro-2H-pyran-2-yl)oxy)-16-ethyl-4-hydroxy-
15-((((2R,3R,4R,5R,6R)-5-hydroxy-3,4-dimethoxy-
6-methyltetrahydro-2H-pyran-2-yl)oxy)methyl)-7-
(2-(isoindolin-2-yl)ethyl)-5,9,13-
trimethyloxacyclohexadeca-11,13-diene-2,10-dione

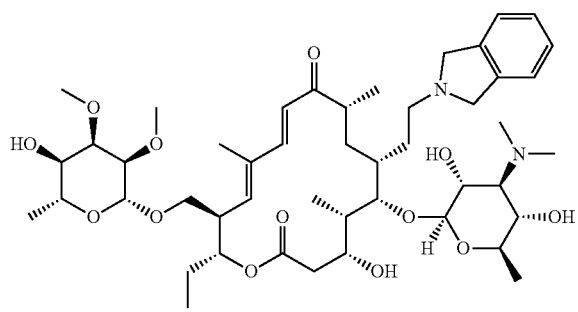 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2Cc3ccccc3C2)C[C@@H](C)C(=O)/C=C/C(C)=C/[C@@H]1CO[C@@H]1O[C@H](C)[C@@H](O)[C@@H](OC)[C@H]1OC]

To a stirred solution of tylosin (9.5 g, 0.011 mol) and isoindoline (3.7 g, 0.031 mol) in 1,4-dioxane (10 ml) was added formic acid (2.7 g, 0.059 mol), the reaction was heated at 70° C. for 2 hours. After completion the reaction was concentrated in vacuo, and the residue was dissolved in 30 ml water, basified with 20% aqueous sodium hydroxide solution to pH 9-10, the resulting white precipitate was filtered and washed with diethylether and petroleumether, dried in vacuo to afford the crude title compound (9.8 g). Mass Calcd: 874.52, Found: 893.50 (M+H$_3$O$^+$).

Example 10

Intermediate 10

(4R,5S,6S,7R,9R,11E,13E,15R,16R)-6-(((2R,3R,4S,
5S,6R)-4-(dimethylamino)-3,5-dihydroxy-6-methyl-
tetrahydro-2H-pyran-2-yl)oxy)-16-ethyl-4-hydroxy-
15-(hydroxymethyl)-7-(2-(isoindolin-2-yl)ethyl)-5,9,
13-trimethyloxacyclohexadeca-11,13-diene-2,10-
dione

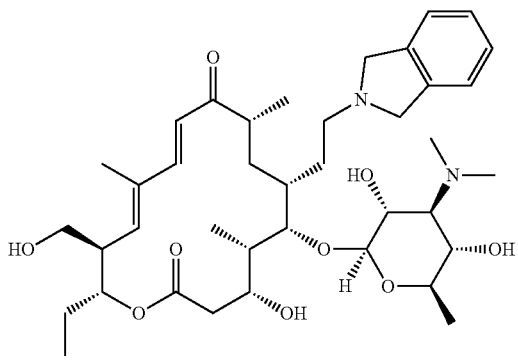 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2Cc3ccccc3C2)C[C@@H](C)C(=O)/C=C/C(C)=C/[C@@H]1CO]

A solution of Intermediate 9 (9.8 g, crude, ~0.011 mol) in hydrobromic acid (45 ml) and water (50 ml) was stirred at 58° C. for 3.5 hours. The mixture was cooled to room temperature and was filtered. The filtrate with basified with 30% sodium hydroxide solution to pH 9-10, the resulting precipitate was washed with petroleumether and filtered. The solid crude product was taken in 30 ml dichloromethane, dried over anhydrous Na$_2$SO$_4$ (10 g) and MgSO$_4$ (10 g) and filtered. The title compound in the filtrate was used directly for the next reaction. Mass Calcd: 700.43, Found: 719.40 (M+H$_3$O$^+$).

Example 11

Intermediate 11

(4R,5S,6S,7R,9R,11E,13E,15S,16R)-6-(((2R,3R,4S,
5S,6R)-4-(dimethylamino)-3,5-dihydroxy-6-methyl-
tetrahydro-2H-pyran-2-yl)oxy)-16-ethyl-4-hydroxy-
15-(iodomethyl)-7-(2-(isoindolin-2-yl)ethyl)-5,9,13-
trimethyloxacyclohexadeca-11,13-diene-2,10-dione

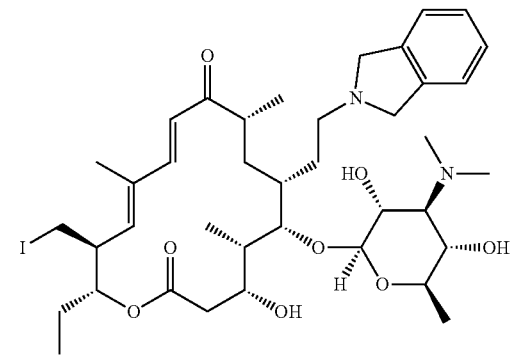 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2Cc3ccccc3C2)C[C@@H](C)C(=O)/C=C/C(C)=C/[C@@H]1CI]

To a solution of Intermediate 10 in dichloromethane (30 ml) in an ice bath was added triphenylphosphine (4.2 g, 0.016 mol), pyridine (2.5 g, 0.033 mol), and iodine (4.4 g, 0.017 mol) portionwise while maintaining the reaction temperature under 15±3° C. The reaction was continued at 20° C. for 3.5 hours and was filtered, the filtrate was extracted twice with 25 ml of concentrated hydrochloric acid, and the combined aqueous layer was basified with 30% sodium hydroxide solution to pH 9-10, the resulting off-white precipitate was filtered and dried to afford the title compound. Mass Calcd: 810.33, Found: 811.20 (M+H$^{3o}$).

Example 12

Compounds 12a-12d

Compounds 12a-12d were prepared from Intermediate 11 using Method B as described in Example 4.

| Cmpd # | Compound Name | Structure | MS |
|---|---|---|---|
| 12a | (4R,5S,6S,7R,9R,11E,13E,15R,16R)-15-((benzyl(methyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-7-(2-(isoindolin-2-yl)ethyl)-5,9,13-trimethyloxacyclohexadeca-11,13-diene-2,10-dione | 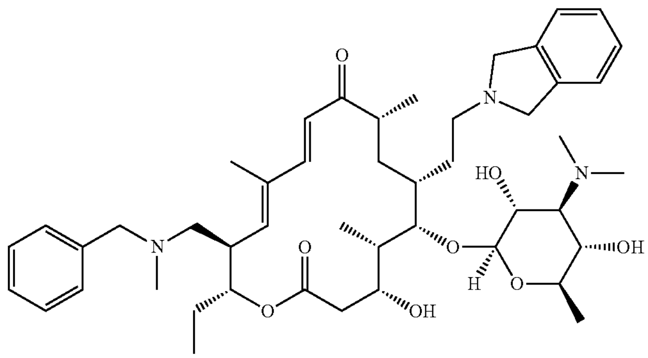 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2Cc3ccccc3C2)C[C@@H](C)C(=O)/C=C/C(C)=C/[C@@H]1CN(C)Cc1ccccc1] | 804.40 (M + H+) |
| 12b | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-16-ethyl-4-hydroxy-7-(2-(isoindolin-2-yl)ethyl)-5,9,13-trimethyl-15-(piperidin-1-ylmethyl)oxacyclohexadeca-11,13-diene-2,10-dione | 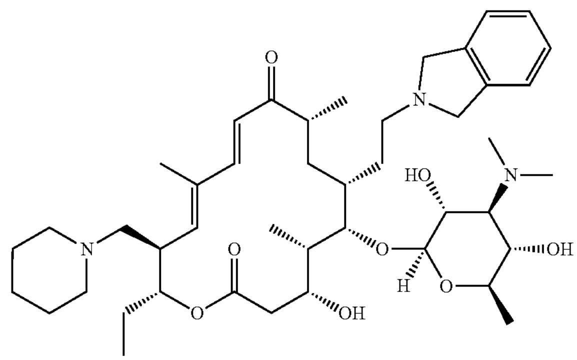 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2Cc3ccccc3C2)C[C@@H](C)C(=O)/C=C/C(C)=C/[C@@H]1CN1CCCCC1] | 768.45 (M + H+) |
| 12c | (4R,5S,6S,7R,9R,11E,13E,15R,16R)-15-((diethylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-7-(2-(isoindolin-2-yl)ethyl)-5,9,13-trimethyloxacyclohexadeca-11,13-diene-2,10-dione | 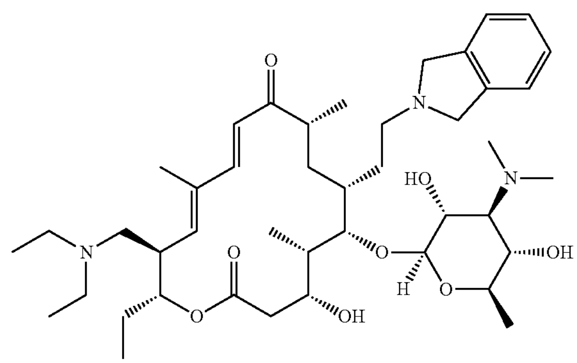 [SMILES: CC[C@H]1OC(=O)C[C@@H](O)[C@H](C)[C@@H](O[C@@H]2O[C@H](C)[C@@H](O)[C@H](N(C)C)[C@H]2O)[C@@H](CCN2Cc3ccccc3C2)C[C@@H](C)C(=O)/C=C/C(C)=C/[C@@H]1CN(CC)CC] | 756.35 (M + H+) |
| 12d | (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-15-((3,5-dimethylpiperidin-1-yl)methyl)-16-ethyl-4-hydroxy-7-(2-(isoindolin-2-yl)ethyl)-5,9,13-trimethyloxacyclohexadeca-11,13-diene-2,10-dione | 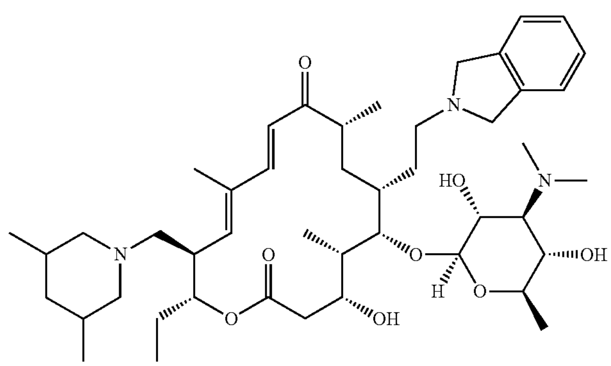 | 796.40 (M + H+) |

Antibacterial Activity Testing

The compounds of the invention inhibit the growth of pathogenic bacteria, including gram-positive bacteria, certain gram-negative bacteria, such as *Pasteurella* species, and Mycoplasma species. The minimal inhibitory concentrations (MIC's) at which illustrative compounds inhibit certain bacteria are given in Table I and Table II. The MIC's in Table I and Table II were determined by standard agar-dilution assays or broth-dilution microtiter test.

TABLE I

Antibacterial activity testing results (mcg/ml)

| Strain | 4a | 4b | 4c | 4d | 4e | 4f | 4g | 4h | Tylosin | Tilmicosin | Zuprevo |
|---|---|---|---|---|---|---|---|---|---|---|---|
| A | 32 | 32 | 64 | >256 | 256 | 16 | 256 | 64 | 16 | 32 | 64 |
| B | 32 | 32 | 128 | >256 | 256 | 64 | 256 | 64 | 8 | 32 | 64 |
| C | 0.5 | 1 | 4 | 256 | 32 | <0.12 | <0.12 | 16 | 32 | 8 | 1 |
| D | 0.5 | 0.25 | 4 | 128 | 16 | 0.12 | 32 | 2 | 32 | 0.5 | 1 |
| E | 8 | 8 | 16 | >256 | 256 | 4 | 256 | 16 | 256 | 16 | 4 |
| F | 4 | 4 | 16 | >256 | 256 | 4 | 256 | 16 | 256 | 8 | 4 |
| G | >256 | >256 | >256 | >256 | 256 | 128 | >256 | 256 | >256 | >256 | >256 |
| H | 4 | 16 | 64 | 256 | 64 | 2 | 128 | 64 | 2 | 0.5 | 256 |
| I | 4 | 8 | 32 | >256 | >256 | 4 | 128 | 32 | >256 | 32 | 8 |
| J | 32 | 32 | 128 | >256 | >256 | 32 | >256 | 128 | >256 | 64 | 32 |
| K | >256 | >256 | >256 | >256 | >256 | >256 | >256 | >256 | >256 | >256 | >256 |
| L | 0.5 | 1 | 2 | 64 | 64 | <0.12 | 32 | 2 | <0.12 | 0.5 | 0.5 |
| M | 8 | 16 | 256 | >256 | 256 | 0.5 | >256 | 32 | 2 | 8 | 256 |

A: *Actinobacillus pleuropneumoniae* serotype 1; B: *Actinobacillus pleuropneumoniae* serotype 7; C: *Pasteurella* 8217; D: *Pasteurella* 8229; E: *Escherichia coli* IN-F6-7; F: *Escherichia coli* 25922 (QC strain); G: *Staphylococcus aureus* 5-1; H: *Staphylococcus aureus* 29213 (QC strain); I: *salmonella* LD4-8; J: *Klebsiella pneumoniae* 3753; K: *Klebsiella pneumoniae* 3699; L: *Streptococcus pneumoniae* 2349; M: *Streptococcus pneumoniae* 49619 (QC strain).

TABLE II

Mycoplasma susceptibility testing results (mcg/ml)

| | MIC | | |
|---|---|---|---|
| Compound # | *M. hyorinis* BTS-7 | *M. gallisepticum* S6 | *M. gallisepticum* BG44T |
| 4a | 62.5 | <0.12 | <0.12 |
| 4b | 15.6 | 0.49 | <0.12 |
| 4c | 31.25 | 15.63 | 7.82 |
| 4f | 0.98 | 0.24 | <0.12 |
| 4i | 15.63 | <0.12 | <0.12 |
| 4j | 0.49 | <0.12 | <0.12 |
| 8a | 3.91 | <0.12 | <0.12 |
| 8b | 125 | 3.91 | 0.98 |
| 8c | 125 | 15.63 | 7.82 |
| 12a | 15.63 | <0.12 | <0.12 |
| 12b | 3.91 | <0.12 | <0.12 |
| 12c | 7.82 | <0.12 | <0.12 |
| 12d | 3.91 | <0.12 | <0.12 |
| Tylosin | 1.95 | <0.12 | <0.12 |
| Tilmicosin | 3.91 | <0.12 | <0.12 |
| Zuprevo | 1.95 | <0.12 | <0.12 |

What is claimed is:

1. A compound having Formula I, its enantiomers, diastereoisomers, tautomers or a pharmaceutically acceptable salt thereof:

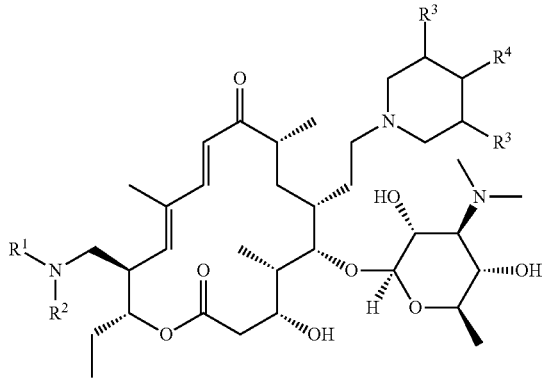

Formula I

Wherein:

$R^1$ is optionally substituted $C_{1-6}$ alkyl or $C_{3-8}$ cycloalkyl, where the substituent is selected from the group consisting of aryl and hydroxyl;

$R^2$ is hydrogen, optionally substituted $C_{1-6}$ alkyl or $C_{3-8}$ cycloalkyl, where the substituent is selected from the group consisting of aryl and hydroxyl; and $R^3$ and $R^4$ are independently selected from the group consisting of hydrogen and $C_{1-3}$ alkyl.

2. A compound or pharmaceutically acceptable salt thereof according to claim 1 wherein:

$R^1$ is optionally substituted $C_{1-4}$ alkyl or $C_{3-8}$ cycloalkyl, where the substituent is selected from the group consisting of benzene and hydroxyl;

$R^2$ is hydrogen or an optionally substituted $C_{1-4}$ alkyl group, where the substituent is selected from the group consisting of benzene and hydroxyl.

3. A compound or pharmaceutically acceptable salt thereof according to claim 2 wherein:

$R^1$ is ethyl, n-propyl, isopropyl, butyl, benzyl, 2-hydroxyethyl, 2-pyridylmethyl, 3-pyridylmethyl, 4-pyridylmethyl, or cyclohexyl;

$R^2$ is hydrogen, methyl, ethyl, n-propyl, isopropyl, n-butyl or 2-hydroxyethyl.

4. A compound or pharmaceutically acceptable salt thereof according to claim 1 wherein:

$R^3$ and $R^4$ are independently selected from the group consisting of hydrogen and methyl.

5. A compound or pharmaceutically acceptable salt thereof according to claim 1 selected from the group consisting of:

(4R,5S,6S,7R,9R,11E,13E,15R,16R)-15-((diethylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione;
(4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-15-((dipropylamino)methyl)-16-ethyl-4-hydroxy-5,9,13-trimethyl-7-(2-(piperidin-1-yl)ethyl)oxacyclohexadeca-11,13-diene-2,10-dione;
(4R,5S,6S,7R,9R,11E,13E,15R,16R)-15-((butylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13- trimethyl-7-(2-(piperidin-1-yl)ethyl)oxacyclohexadeca-11,13-diene-2,10-dione; (4R,5S,6S,7R,9R,11E,13E,15R,16R)-15-((benzylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((benzyl(methyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((bis(2-hydroxyethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((cyclohexylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((benzyl(ethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((benzyl(isopropyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; and (4R,5S,6S,7R,9R,11E,13E,15R,16R)-15-((benzyl(isopropyl)amino)methyl)-6-(((2R,3R,4S,5S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-5,9,13-trimethyloxacyclohexadeca-11,13-diene-2,10-dione.

6. A pharmaceutical composition comprising as active ingredient a therapeutically effective amount of a compound according to claim 1 and a pharmaceutically acceptable adjuvant, diluents or carrier.

7. A pharmaceutical composition according to claim 6 wherein the compound is selected from the group consisting of:

(4R,5S,6S,7R,9R,11E,13E,15R,16R)-15-((diethylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-6-(((2R,3R,4S,5S,6R)-4-(dimethylamino)-3,5-dihydroxy-6-methyltetrahydro-2H-pyran-2-yl)oxy)-15-((dipropylamino)methyl)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((butylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((benzylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((benzyl(methyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((bis(2-hydroxyethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((cyclohexylamino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((benzyl(ethyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; (4R,5S,6S,7R,9R,11E,13E,15R,16R)-15-((benzyl(isopropyl)amino)methyl)-6-(((2R,3R,4S,5S,6R)-4-(dimethylamino)-3,5-dihydroxy-6-methyltetrahydro-2H-pyran-2-yl)oxy)-16-ethyl-4-hydroxy-5,9,13-trimethyl-7-(2-(piperidin-1-yl)ethyl)oxacyclohexadeca-11,13-diene-2,10-dione; and (4R,5S,6S,7R,9R,11E,13E,15R,16R)-15-((benzyl(isopropyl)amino)methyl)-6-(((2R,3R,4 S, S,6R)-4-(dimethylamino)-3,5-dihydroxy-6-methyltetrahydro-2H-pyran-2-yl)oxy)-7-(2-(3,5-dimethylpiperidin-1-yl)ethyl)-16-ethyl-4-hydroxy-5,9,13-trimethyloxacyclohexadeca-11,13-diene-2,10-dione.

* * * * *